US008450347B2

(12) United States Patent
Hageman et al.

(10) Patent No.: US 8,450,347 B2
(45) Date of Patent: *May 28, 2013

(54) COMPOSITION FOR RELIEVING DISCOMFORT

(75) Inventors: Robert Johan Joseph Hageman, Vaddinxveen (NL); Jacob Geert Bindels, Zoethermeer (NL)

(73) Assignee: N.V. Nutricia, Ma Zoetermeer (NL)

( * ) Notice: Subject to any disclaimer, the term of this patent is extended or adjusted under 35 U.S.C. 154(b) by 879 days.

This patent is subject to a terminal disclaimer.

(21) Appl. No.: 12/033,379

(22) Filed: Feb. 19, 2008

(65) Prior Publication Data

US 2008/0145451 A1    Jun. 19, 2008

Related U.S. Application Data

(60) Division of application No. 11/125,201, filed on May 10, 2005, now Pat. No. 8,124,585, which is a continuation-in-part of application No. 09/889,793, filed as application No. PCT/NL00/00042 on Jan. 20, 2000, now Pat. No. 6,900,180.

(30) Foreign Application Priority Data

Jan. 20, 1999  (EP) .................................... 99200166
Apr. 29, 1999  (EP) .................................... 99201359

(51) Int. Cl.
*A61K 31/4375*  (2006.01)
*A61K 31/4415*  (2006.01)
*C07D 213/67*   (2006.01)
*C07D 475/04*   (2006.01)

(52) U.S. Cl.
USPC ........... 514/345; 514/249; 514/351; 514/350; 544/258; 546/298; 546/300; 546/290

(58) Field of Classification Search
USPC ............... 514/345, 249, 351, 350; 546/298, 546/300, 290; 544/258
See application file for complete search history.

(56) References Cited

U.S. PATENT DOCUMENTS

| | | | |
|---|---|---|---|
| 3,930,039 A | 12/1975 | Kuipers | |
| 4,491,589 A | 1/1985 | Dell et al. | |
| 4,753,926 A | 6/1988 | Lucas et al. | |
| 4,920,098 A | 4/1990 | Cotter et al. | |
| 5,053,429 A | 10/1991 | Hirsch et al. | |
| 5,075,290 A | 12/1991 | Findley et al. | |
| 5,132,113 A | 7/1992 | Luca | |
| 5,292,538 A | 3/1994 | Paul et al. | |
| 5,451,412 A * | 9/1995 | Bounous et al. | 424/535 |
| 5,500,225 A | 3/1996 | Laudon et al. | |
| 5,545,670 A | 8/1996 | Bissbort et al. | |
| 5,549,905 A | 8/1996 | Mark et al. | |
| 5,631,271 A | 5/1997 | Serfontein | |
| 5,635,199 A | 6/1997 | Trimbo et al. | |
| 5,691,325 A | 11/1997 | Sandyk | |
| 5,700,590 A | 12/1997 | Masor et al. | |
| 5,728,678 A | 3/1998 | Trimbo et al. | |
| 5,792,754 A | 8/1998 | Green et al. | |
| 5,801,159 A | 9/1998 | Miller et al. | |
| 5,817,695 A | 10/1998 | Pellico | |
| 5,922,766 A * | 7/1999 | Acosta et al. | 514/561 |
| 6,077,828 A * | 6/2000 | Abbruzzese et al. | 514/21 |
| 6,200,607 B1 * | 3/2001 | Bridgeman | 424/643 |
| 6,221,836 B1 | 4/2001 | Beale et al. | |
| 6,420,342 B1 | 7/2002 | Hageman et al. | |
| 6,475,539 B1 | 11/2002 | DeWille et al. | |
| 6,548,483 B2 * | 4/2003 | Hageman et al. | 514/23 |
| 6,613,367 B1 | 9/2003 | Wells et al. | |
| 6,660,293 B2 | 12/2003 | Giordano et al. | |
| 6,900,180 B1 | 5/2005 | Hageman et al. | |
| 7,560,447 B2 * | 7/2009 | Kiliaan et al. | 514/165 |
| 7,867,541 B2 | 1/2011 | McMahon et al. | |
| 2002/0147153 A1 | 10/2002 | Bell et al. | |
| 2002/0155104 A1 | 10/2002 | Munn et al. | |
| 2007/0231402 A1 | 10/2007 | Girsh | |
| 2008/0193561 A1 * | 8/2008 | Kiliaan et al. | 424/630 |
| 2008/0317868 A1 * | 12/2008 | Hageman et al. | 424/639 |

FOREIGN PATENT DOCUMENTS

| | | |
|---|---|---|
| DE | 41 30 284 A1 | 3/1993 |
| DE | 43 26 675 | 2/1995 |
| DE | 4326675 A1 * | 2/1995 |
| EP | 0 769 1 B1 | 1/1984 |
| EP | 0 144 051 B1 | 1/1990 |
| EP | 0 463 154 A1 | 1/1992 |
| EP | 0 721 742 | 7/1996 |
| IT | 23959 | 11/1983 |
| WO | WO 87/01590 | 3/1987 |

(Continued)

OTHER PUBLICATIONS

Dijkstra et al., "Care Dependency and Survival Among Female Patients with Alzheimer's Disease: A Two-Year Follow-Up" Croatian Medical Journal (1998) vol. 39 No. 3, pp. 1-6.*

(Continued)

*Primary Examiner* — Eric S Olson
(74) *Attorney, Agent, or Firm* — Gilberto M. Villacorta; Sunit Talapatra; Foley & Lardner LLP

(57) ABSTRACT

The invention relates to a method of controlling feelings of pain in infants or diseased or elderly persons using a complete nutrition or a nutritional supplement. The method comprises administering increased levels of folic acid, vitamin B6 and vitamin B12 or their functional equivalents.

16 Claims, No Drawings

FOREIGN PATENT DOCUMENTS

| | | |
|---|---|---|
| WO | WO-91/10441 A1 | 7/1991 |
| WO | WO 92/15311 | 11/1992 |
| WO | WO-96/22774 A2 | 8/1996 |
| WO | WO-98/14204 A1 | 4/1998 |

OTHER PUBLICATIONS

Chouinard et al., "Weight Loss, Dysphagia, and Outcome in Advanced Dementia" Dysphagia (1998) vol. 13 pp. 151-155.*
Machine translation of DE4326675 (Etle et al.) above, published Feb. 1995, translated (2010) by Google Translation.*
Fisler et al., "Dietary Obesity: Effects of Drugs and food intake in S 5B/P1 and Osborn-Mendel Rats" Physiology and Behavior (1985) vol. 34, pp. 225-231.
The Merck Manual of Diagnosis and Therapy, Seventeenth Edition, published (1999) by Merck Research Laboratories. Edited by Beers and Berkow, pp. 58-62.
Cazzola et al., "5-HT Modifiers as a potential treatment of asthma" Trends in Pharmacological Science (2000) Vo. 21, No. 1, pp. 13-16.
Giron-Caro et al., "Melatonin and beta-endorphin Changes in Children Sensitized to Olive and grass Pollen after Treatment with Specific Immunotherapy" International Archives of Allergy and Immunology (2001), Vo. 126, pp. 91-96.
Abou-Saleh et al., "Psychiatric Progress—The Biology of Folate in Depression: Implications for Nutritional Hypotheses of the Psychoses," J. Psychiat. Res., vol. 20, No. 2, 1986, pp. 91-101.
Andrassy et al., "Nutritional Support of the Pediatric Oncology Patient," Nutrition, vol. 14, No. 1, 1998, pp. 124-129.
Bernstein, A., "Vitamin $B_6$ in Clinical Neurology," Annals New York Academy of Sciences, 1990, pp. 250-260.
Bhagavan et al., "The Effect of Pyridoxine Hydrochloride on Blood Serotonin and Pyridoxal Phosphate Contents in Hyperactive Children," The American Academy of Pediatrics, vol. 55, Issue 3, 1975, pp. 437-441.
Dakshinamurti, et al., "Influence of B Vitamins on Binding Properties of Serotonin Receptors in the CNS of Rats," Klin Wochenschr, vol. 68(2), Jan. 1990, pp. 142-145.
Dakshinamurti et al., "Neurobiology of Pyridoxine," Annals of the New York Academy of Sciences, vol. 585, 1990, pp. 128-144.
Dakshinamurti, K., Annals of the New York Academy of Sciences—Vitamin $B_6$, vol. 585, New York, New York, 1990, 7 pages. (TOC).
Drug information for Travosol® amino acid composition, downloaded from www.rxlist.com, last updated May 5, 2009, 3 pages.
Gonzalez et al., "Brief Communication: Effect of Naturally Occurring Sugars on Ehrlich Ascites Tumor Growth in Mice," J. National Cancer Inst., 1977, vol. 58, No. 5, pp. 1519-1522.
Grant et al., Enternal & Parenteral Nutrition—A Clinical Handbook, Blackwell Scientific Publications, Second Edition, 1987, 8 pages.
Hanning et al., "Protein Metabolism and Growth of Term Infants in Response to a Reduced-Protein, 40:60 Whey: Casein Formula With Added Tryptophan[1-3]," American Society for Clinical Nutrition, 1992, vol. 56, pp. 1004-1011.
Honma, et al., "Effects of Vitamin B12 on Plasma Melatonin Rhythm in Humans: Increased Light Sensitivity Phase-Advances the Circadian Clock?," Experientia, Aug. 1992, vol. 48 (8), pp. 716-720.
Jurna et al., "Acute Effects of Vitamin B6 and Fixed Combinations of Vitamin B1, B6 and B12 on Nociceptive Activity Evoked in the Rat Thalamus: Dose-Response Relationship and Combinations With Morphine and Paracetamol," Klin Wochenschr, 1990, vol. 68(2), pp. 129-135.
Jurna, I., "Analgesic and Analgesia-Potentiating Action of B Vitamins," Schmerz, 1998, vol. 12, pp. 136-141.
Kolb, E., "Some New Biochemical Knowledge on the Effect of Nutritional Factors on Brain Function," Z Gesamte Inn Med., vol. 42(24), 1987, pp. 689-695. (abstract only).
McDonough et al., "Whey Protein Concentrate as a Milk Extender," Journal of Dairy Science, vol. 59, No. 1, 1976, pp. 34-40.
Munoz-Hoyos et al., "Pineal Response After Pyridoxine Test in Children," Journal of Neural Transmission, vol. 103, 1996, pp. 833-842.
Nave et al., "Melatonin Improves Evening Napping," Eur J Pharmacol., vol. 275(2), Mar. 1995, pp. 213-216.
Okawa, et al., "Vitamin $B_{12}$ Treatment for Sleep-Wake Rhythm Disorders," Sleep, vol. 13(1), 1990, pp. 15-23.
Parry et al., "Oral Contraceptives and Depressive Symptomatology: Biologic Mechanisms," Comprehensive Psychiatry, vol. 20, Issue 4, Jul.-Aug. 1979, pp. 347-358.
Rompp Chemie Lexikon, definition of "Melatonin", 1998, 4 pages.
Rompp Chemie Lexikon, definition of "Serotonin", 1992, 4 pages.
Rompp Chemie Lexikon, definition of "Serotonin", 1999, 5 pages.
Sandyk, R., "L-Tryptophan in Neuropsychiatric Disorders: A Review," Intern. J. Neuroscience, vol. 67, 1992, pp. 127-144.
Sundararajan et al., "Preparation and Amino Acid Composition of Enzymically Dephosphorylated Casein," Biochemical Journal, vol. 65(2), 1957, pp. 261-266.
Syndromes of Uncertain Origin, The Merck Manual, 18th Edition, 2006, pp. 2740-2741.
The Merck Manual of Diagnosis and Therapy, Seventeenth Edition, published 1999 by Merck Research Laboratories, 2 pages.
The Merck Manual of Diagnosis and Therapy, Sixteenth Edition, published 1992 by Merck Research Laboratories, pp. 1664-1665, 1950-1951, 2002-2003, and 2032-2033.
The Merck Manual, Section 1—Nutritional Disorders 18th Edition, 2006, pp. 1-47.
Young, S.N., The 1989 Borden Award Lecture. "Some Effects of Dietary Components (Amino Acids, Carbohydrate, Folic Acid) on Brain Serotonin Synthesis, Mood, and Behavior," Can J Physiol Pharmacol, vol. 69(7), 1991, pp. 893-903.
Young, Simon N. Ph.D., "The Use of Diet and Dietary Components in the Study of Factors Controlling Affect in Humans: A Review," J Psychiat Neurosci, vol. 18, No. 5, 1993, pp. 235-244.
Zhdanova, I.V., "Sleep-Inducing Effects of Low Doses of Melatonin Ingested in the Evening," Clin. Pharmacol Ther., vol. 57(5), May 1995, pp. 552-558.

* cited by examiner

COMPOSITION FOR RELIEVING DISCOMFORT

This is a divisional application to U.S. application Ser. No. 11/125,201, filed May 10, 2005, which is a continuation-in-part application to U.S. application Ser. No. 09/889,793, now U.S. Pat. No. 6,900,180, filed Oct. 24, 2001, which is the national phase of PCT application PCT/NL00/00042, filed Jan. 20, 2000, which claims priority to foreign applications EP99200166.9, filed Jan. 20, 1999, and EP99201359.9, filed Apr. 29, 1999.

FIELD OF THE INTENTION

The invention is related to pharmaceutical and/or nutritional compositions, including infant formulae, for improving feelings of well-being, compensation of immaturity and problems in the capacity to metabolize tryptophan or tryptophan or for preventing disorders in homeostasis of tryptophan or its metabolites. The nutritional products provide complete nutrition to infants, diseased and elderly people, and their composition is characterised by increased amounts of cofactors. The nutritional products can also be in the form of supplements that provide the cofactors and only a part of the further desirable food components.

BACKGROUND OF THE INVENTION

At present a large part of the population of babies in industrialised countries are fed with specialised infant formulae. It has been reported that consumption of these formulae is associated with several medical problems, such as increased frequency of gastrointestinal problems and decreased immune status. Such problems may occur at young age, but perhaps also at later age, because infants that are exclusively fed with human breast milk would score better on these parameters. It has also been reported that infants that are exclusively fed with these artificial formulae suffer from longer episodes of crying compared to those that are fed with human breast milk. This suggests a general feeling of discomfort due to perhaps hunger, pain or even medical problems. These problems may delay development of the child and produce concerns and practical problems to the parents.

In a first aspect of the invention it is aimed to develop a new infant formula for complete nutrition that decreases the number of crying episodes and promotes sleeping behaviour for the child, especially for infants of young gestational age.

In a second aspect it is also aimed to develop infant formulae that compensate for the relatively small capacity of the (rapidly developing) metabolic systems of the child shortly after birth. This leads to improved health, formation of higher quality new tissue (visual acuity, intellectual capacities, etc.), a better immune status and a decrease in occurrence of periods of increased bilirubin plasma levels (hyperbilirubinaemia or jaundice). Increased bilirubin levels are known to occur relatively often within the first 3 weeks after birth. Some of the negative effects of this disorder have been described in the prior art, including the inhibition by bilirubin of the uptake of the neurotransmitters dopamine and glutamate by the synaptic vesicles and the neurotoxic effects that this disease state may have.

Conventional infant formulae have been developed that mimic the composition of human breast milk to a degree that can be achieved at a reasonable price. These formulae are normally based on cow's milk proteins like casein or mixtures of casein and whey. In case of problems, such as metabolic disorders or allergic reactions, other protein sources are used like hydrolysates or soybean proteins; alternatively the allergic component is replaced by another non-allergenic ingredient. However, the composition of these formulae still differs from that of human breast milk. The relatively low levels of tryptophan and cysteine/cystine can be compensated for by increasing the amount of protein in the product. However, this increases the amount of threonine to very high levels and increases the costs of the formulae. Also the imbalances with regard to the ratio of tryptophan to the sum of the large neutral amino acids will be maintained.

In a further aspect, the invention is related to the use of folic acid, and at least one of vitamin B12 and B6, or their functional analogues in the manufacture of compositions for the prevention and/or treatment of specific neurological disorders. The invention also covers the products that are obtained by such use. Products according to the invention will be effective in improving sleep behaviour, insomnia and mood, in decreasing feelings of fear, pain, restlessness and depression and increasing feelings of wellbeing. In addition, these symptoms as related to neurodegenerative disorders like Alzheimer, Parkinson and schizophrenia will decrease, though the disease itself is not cured. Also, the products can be helpful in the prevention and/or treatment of the symptoms that are typically associated with restless legs syndrome, myoclonus (a disorder that is often accompanied by muscle contractions and seizures), Gilles de la Tourette, Carpal tunnel syndrome, phenylketonuria, multiple sclerosis, analgesia, epilepsy, mania, ADHD, and psychiatric disorders associated with ageing. Relatively large parts of the population suffer from one of these disorders. Application of common drug therapy may result in undesired side effects, such as addiction and gradual loss of affectivity, and may lead to functional deficiencies of food components. So there is a need for a pharmaceutical or nutritional formulation that helps prevent or treat these disorders and does not result in these side effects.

Sandyk, R., reported in *Intern. J. Neuroscience,* 1992, 67, 127-144 that several, but not all, of these disorders were associated with decreased serotonin levels in the brain and reviewed some of the relevant literature about the use of tryptophan to restore serotonin levels in the brain.

In a next aspect of the invention the products according to the invention aim to improve sleep behaviour, insomnia and mood, in decreasing feelings of fear, pain, restlessness and depression and increasing feelings of well-being during many immune-related diseases. Immune-related diseases are diseases, in which the recognition of cells is hampered or disturbed and thus results in an inappropriate reaction against undesired cells or antigens. Examples of such diseases are several infectious diseases and cancers in which too weak of a reaction occurs against mutated or infected cells and many autoimmune diseases, in which relatively mild antigens trigger a disproportional strong reaction.

In US 2002/0155104 such an imparted tryptophan metabolism is recognized in cells that are infected by specific viruses. By influencing the activity of indoleamine 2,3-dioxygenase (IDO), in particular by administering inhibitors of IDO, '104 aims to decrease or increase tryptophan levels to levels below or above physiological levels. The beneficial effects of protein composition or vitamins are not contemplated.

The inventors theorize that during all the immune-related diseases as mentioned above local tryptophan homeostasis is significantly disturbed. By mutated or infected cells, eg those infected by HIV, cytomegalovirus and Herpes, significant amounts of cytokines will be released which increase tryptophan catabolism significantly. The increase in tryptophan metabolism also decreases systemic plasma tryptophan levels and increases at least locally levels of kynurenine, and their metabolites like quinolinates, kynurenates, anthranilates and niacin or nicotinamide. Also formate is released and endogenous local levels of total nicotinamide nucleotides (predominantly the sum of NAD+, NADP+, NADPH and NADH) as well as serotonin are decreased. Such disturbances of total tryptophan metabolism, which includes serotonin and melatonin homeostasis leads to a locally and strongly compromised immune function, especially against infected and mutated cells of the body, which could result in metastasis or rapid tumor growth and rapid infection rates and thus leads to fatigue, decreased stamina, anorexia and increased feelings of pain.

Also in so called autoimmune diseases, like rheumatoid arthritis, Crohn's Disease, diabetes type 1, lupus erythematosus, multiple sclerosis, scleroderma, psoriasis, etc, total tryptophan metabolism appears to be imparted. In these situations tryptophan catabolism does not function as an appropriate inhibitor of the antigenic reaction. Endogenous and exogenous products, which are recognized as antigens therefore trigger a very strong response, which includes itching, sensations of burning, pressure, and varying degrees of pain, changing from vague pain to smarting—and aggressive pains. Food and non-food allergies may also result in a wide range of systemic reactions which include diarrhea, airway obstruction and even shock. In autoimmune diseases, dependant on the nature of the disease, a gradual destruction of tissue may be observed, as well as several symptoms that are typical for the autoimmune disease.

The inventors further consider that these disorders are associated not only with a disorder in serotonin levels, but also with the melatonin levels in the brain, the presence of pterines and folate in the brain and the functioning of tryptophan metabolism and the methylating system in the body. The latter may become evident by abnormal systemic and local adenosine and/or tryptophan levels. Because relatively very little serotonin or melatonin is present in the normal diet, most endogenous amounts must originate from biosynthesis. An increase in the brain levels of both serotonin and melatonin can therefore only be achieved by increasing the metabolic capacity of the serotoninergic neurons. An increase of the brain levels of both serotonin and melatonin and the presence of reduced folic acid and pterins in the brain would lead to a relief of the clinical problems.

Sandyk disclosed that in some cases administration of an effective amount of the natural precursor of serotonin, tryptophan, could lead to increased levels of serotonin in brain tissue. This idea was also subject of a number of other publications, which appeared in the past.

WO 87/01590 (=EP-A-238533, Kreitzman) discloses a slimming diet for adults that provides per day less than 1000 kcal (so less than 14 kcal/kgbw·d; less than 700 kcal/day is preferred), less than 100 g protein (which results in less than 1.4 g protein per kgbw per day for a 70 kg person; always more than 30 g and less than 46 g protein is preferred) and more than 0.5 g tryptophan (more than 3 g is preferred). The product is unsuitable for feeding infants due to too high protein levels and potential toxicity of the amount of tryptophan that is included. The product should also not be used for combating obesity of the infant.

EP-A-007691 (Wurtman) discloses a formula for suppression of appetite for carbohydrates in adults, which comprises tryptophan, in an amount of 10-100 mg per kgbw·d, and carbohydrates, but no branched-chain amino acids. The ratio of the amounts of tryptophan and carbohydrates in the formula must be 1:3-50. The product is unsuitable for use in infants, because infants require branched chain amino acids at young age for growth.

U.S. Pat. No. 5,053,429 (Hirsch) discloses a method for treating pain in a subject comprising administering to the subject in dosage form an effective relieving amount of at least one specific methionine compound, the unnatural d-isomer which does not occur in proteins, and optionally at least one of 0.3-30 ug vitamin B12, 0.2-20 mg vitamin B6 and 40-4000 ug folic acid. The methionine compound is administered in an amount of 1.0-10 g per 70 kg body weight.

Jurna reviewed in Schmerz 1998, 12, 136-141 the analgesic properties of B-vitamins. Administration of very high doses of each of specific B-vitamins (20-200 mg vitamin B1 resulted in a "trend"; 100-500 mg vitamin B6 during carpal tunnel syndrome or 5-10 mg vitamin B12 during osteoarthritis resulted in an analgesic effect, though others have criticised the research that has been done on the role of vitamin B6 in carpal tunnel syndrome) or in combination (100-300 mg vitamin B1, 100-600 mg vitamin B6 and 0.6-1 mg vitamin B12 per day during diabetic neuropathies) resulted in an analgesic effect. Chronic administering of such high dose of vitamin B6 was found to damage neurons. Folic acid and proteins were not considered.

WO 91/10441 (=EP-A-463154) discloses compositions comprising polypeptides containing more than 2.2% tryptophan as well as arginine or ornithine for providing a "serotinergic effect". The product is developed for combating obesity in adults and treating feelings of depression. Preferably α-lactalbumin is used as a source of tryptophan, which possesses a high ratio of tryptophan to large neutral amino acids plus methionine. Vegetable proteins are suggested as attractive ingredients, because of their relatively high amount of arginine and relatively low levels of phenylalanine and tyrosine. The latter two amino acids are however essential amino acids and recommended daily intakes should be ensured.

WO 98/14204 discloses the use of α-lactalbumin as nutritional complement or medicine for regulating sleep, especially when a jet lag is observed. Consumption of 100 mg and 250 mg α-lactalbumin is claimed to be effective in adults. No relation is made to use in infants nor is indicated that vitamins might play a role in regulating sleep. Alpha-lactalbumin was shown to have a value of the ratio of tryptophan to the sum of the large neutral amino acids is about 0.074 and that of the ratio Cys to Trp equals about 1.47, while the amount of tryptophan is relatively high (about 3.0%).

Heine discloses the use of hydrolysed β-lactalbumin as protein source in infant formulae in DE-A-4130284. Use of this protein hydrolysate was claimed in order to achieve a clear separation with β-lactoglobulin and thus administer a better-balanced composition with regard to threonine, tryptophan and cysteine/cystine. No reference was made to specific positive effects that can be obtained by using intact α-lactalbumin with regard to feelings of well-being nor the support of insufficiently functioning metabolic systems by using the products of the invention. No indication is given that folic acid, vitamin B12 and B6 play a crucial role in these respects. The products disclosed by Heine are also more expensive and have a worse taste compared to the products of the present invention.

After consumption of carbohydrates, insulin is released from the pancreas. This latter component is known to reverse the catabolic processes in the body, that may have resulted from a period of starvation prior to the (re)feeding of the child, into anabolic processes. As long as sufficient glucose is present in the plasma, plasma insulin levels remain sufficiently high to prevent catabolism of (in particular muscle) tissue and the resulting release of branched chain amino acids (BCAA, valine, isoleucine and leucine). In a further aspect, the invention is therefore aimed at developing formulae that provide an insulin response on a short term, with a sufficient longer-term effect as well.

Infants, especially those of young gestational age, are extremely sensitive to consumption of excess amounts of food components and imbalances in the consumption pattern of these components, predominantly due to their relatively low metabolic and clearance capacity. This is caused by inherited problems and immaturity of their enzymatic systems and the small capacity of their organs. Infants are also sensitive to imbalances in neurotransmitter levels in the brain. It is therefore dangerous to transfer concepts that are developed for healthy adults to infant formulae. The composition of human breast milk is therefore mostly taken as "golden standard". In another aspect of the invention, a nutritional product is aimed at that does not cause any toxic reactions in normal use and to deviate as little from the golden standard as is justified.

It is important to recognise that all the aspects as mentioned above must be achieved at the same time, in order to improve well-being satisfactorily without causing negative effects to the child.

Also elderly and diseased people may suffer from an imparted metabolic capacity and especially the group having neurodegenerative disorders, and developed viral infections of autoimmune diseases and cancer patients should not be exposed to unbalanced food.

According to the prior art, relatively high doses of tryptophan have to be administered, optionally in the relative absence of large neutral amino acids and accompanied with digestible carbohydrates, in order to see clinical benefits. This approach leads to several problems. In some patients no or very little effect is observed. Administering high doses of tryptophan may lead to undesired side-effects, especially in those patients that have a low metabolic capacity or are deficient in certain vitamins or minerals. Examples of these patients are persons that are at risk for or are suffering from diabetes mellitus or bladder cancer, persons that are subjected to drug therapy, persons suffering of renal problems, young infants and elderly persons. Also, it appeared to be very difficult to estimate for a particular person the exact requirement of tryptophan for obtaining optimal serotonin levels and it is unknown how high these desirable serotonin levels are.

It has now been found that the restoration of the patient's capacity to metabolise tryptophan to serotonin and especially melatonin, is an approach that does not demonstrate the above-mentioned disadvantages. It allows the natural mechanisms to regulate endogenous levels, without subjecting the organism to high levels of potentially toxic tryptophan.

This can be achieved by administering extra amounts of certain cofactors, at least folic acid, vitamin B12 and vitamin B6. In this situation it is often not required to supplete tryptophan; however, in those cases that persons are deficient in tryptophan, or suffer from largely increased catabolism of tryptophan administration of relatively little amounts of tryptophan already gives significant improvement of the clinical symptoms.

In cases where a patient has a limited capacity for serotonin biosynthesis, e.g. by damage to tissue that is rich in serotoninergic neurons or due to an inherited disorder, administration of cofactors appeared to increase serotonin and melatonin levels in the brain, if a certain basal level of tryptophan was available.

It was found that the cofactors of interest are at least folate, and one of vitamin B6 and vitamin B12 or their functional equivalents. In addition it may be required to administer riboflavin, thiamine and niacin, or their functional equivalents.

The biochemical roles of folate, vitamin B6 and B12 and many of their equivalents are described in the art. To the best of the knowledge of the inventors, it is nowhere described or indicated that consumption of the combination of these vitamins, in a nutritional product that comprises only natural materials like proteins and digestible carbohydrates, is crucial for prevention or treatment of pain, anorexia, itching burning and pressure, fatigue and loss of stamina in persons that are of age above 60 years or suffer from one or more diseases or disorders. It was found that the restrictions in protein and carbohydrates composition, that are present for infant formulae, necessitate the increase in these vitamins in order to have an optimal effect. It is also not earlier disclosed that inclusion of these vitamins in the amounts as claimed, significantly enlarges the group of infants that benefit from such infant formulae, especially with regard to increase of well-being, the improvement of other serotonin or melatonin-mediated disorders.

Also, the amounts of all three essential vitamins, being folic acid, vitamin B6 and B12 are insufficient in current commercial infant formulae to support biosynthesis and metabolism, including the serotonin metabolism, in the young child.

DETAILED DESCRIPTION OF THE INVENTION

The composition according to the invention to be used for the treatment of pain and related symptoms is characterized by containing a protein fraction and digestible carbohydrates and two or more vitamins from the B group (folate, B6 and B12). The protein fraction has a relatively high tryptophan content. The composition and its use are described in the claims and in more detail below.

The tryptophan-rich source is believed to ensure proper supplementation of tryptophan to guarantee physiological levels of tryptophan in brain, liver, gut epithelium, but also locally near mutated or infected cells. The administration of high levels tryptophan is not obvious as tryptophan metabolites may be toxic on nerve cells and other cells. Vitamins have an effect on tryptophan metabolism by 1 increasing serotonin levels, 2/increasing melatonin and 3/decreasing formate, thereby increasing catabolism rate without inhibiting or upregulating IDO (indoleamine 2,3-dioxygenase), and 4/decreasing putrescine levels.

The optimum concentration of the active components is often expressed as an amount (e.g. weight) per daily dose. For the purpose of this invention it is assumed that an adult will consume 2000 kcal per day and an infant 450 kcal. This allows calculation from daily dose to energy content in the product. It is further assumed that the energy in the product is solely provided by the protein fraction, which includes intact proteins, peptides and free amino acids, the fraction of digestible carbohydrates, which includes digestible mono, di-, oligo- and polysaccharides and can be determined by the standard Englyst method, and the lipid fraction, which includes triglycerides, diglycerides, monoglycerides, free fatty acids, phospholipids, steroids, ceramides and sphingolipids.

In adults, it is preferred that at least 400 µg folate, preferably 500-10,000 µg and more preferably 600-6000 µg folate is included per daily dose. In addition, it is preferred that at least 1.9 µg, preferably 4.8-5000, more preferably 6-540 µg vitamin B12 be included per daily dose. Further, at least 0.3 mg vitamin B6 is required per daily dosage, preferably 3.0-50 and more preferably 3.4-30 mg. Folate is defined as an oxidized or reduced form of folic acid, and derivatives and salts thereof, which include methylated or formylated forms, salts with minerals such as calcium, zinc, magnesium, sodium and potassium, and forms to which one or more glutamate molecules have been attached. Vitamin B12 is considered to be all food grade cobalamines, such as cyanocobalamine, hydroxocobalamine or adenosylcobalamine. Vitamin B6 is defined as all food grade precursors of pyridoxal phosphate, in particular pyridoxine, pyridoxamine and pyridoxal.

In most cases also at least 0.5 mg riboflavin (vitamin B2), 1.0 mg thiamine (vitamin B1) and at least 2 $m^{-1}$ niacin per daily doses is required. The amount of vitamin B1 must be below 90 mg, preferably below 50 mg per daily dose. Deficiencies on the latter components occur relatively often in the above-mentioned groups of patients and these will lead to imparted generation of ATP and reducing power in the form of NAD(P)H. Riboflavin is also required for activating pyridoxal. Low ATP levels are deleterious to the metabolic capacity to methylate and the biosynthetic capacity for melatonin and serotonin.

It is further highly desirable that digestible carbohydrates that can serve as glucose source are included in the product. Examples are glucose polymers, disaccharides like lactose and sucrose. Also, inclusion of monosaccharides like glucose, maltose, fructose, ribose and galactose ensures a continuous supply of reducing equivalents in the form of NADH and improves in some instances the transport of tryptophan from blood into the brain. A product according to the invention should advantageously comprise at least 5 g digestible carbohydrates and preferably more than 10 g on a daily basis. Per 100 kcal (419 kJ) of product, the amount of digestible carbohydrate is in the range of 4-25 g, preferably 6-22 g and more preferably 8-20 g.

The product should further preferably comprise magnesium to improve methylation, and zinc to improve total metabolism of sulfur amino acids. Magnesium also stabilises the NMDA receptor. An overstimulation of the NMDA receptor is associated with many of the above-mentioned disorders and maintenance of an overstimulation of this receptor is claimed to aggravate some of the symptoms that are observed in some of these diseases. Zinc is further involved in the modulation of neurotransmitter receptors. Zinc should best be above 0.7 mg/100 kcal, which results in a daily intake of at least 3.6 mg. Magnesium should best be included in an amount of at least 5 mg/100 kcal, leading to a daily consumption of at least 36 mg. On the other hand, the amounts of calcium and phosphorus should not be too high. Specifically, the weight ratio of Mg+Zn to Ca should be more than 0.08, preferably more than 0.10, and the weight ratio of Mg+Zn to P should be more than 0.2, preferably more than 0.26 (and Ca+Mg+Zn/P>1.9).

The protein fraction preferably provides tryptophan in an amount of 0.05-3 g per daily dose, in particular 0.3-1.2 g. Preferably tryptophan is supplied predominantly in the form of an intact protein. At least 30 wt % of the protein fraction is preferably in the form of intact protein, more preferably 60-100, and most preferably 80-100 wt %. The protein must have an amino acid composition that is characterised by a high ratio of tryptophan/large neutral amino acids, preferably in the range of 0.048-0.2. Preferably the amount of arginine is less than 5 wt %, more preferably 0.4-4.0, most preferably 1.6-3.1 wt %. Methionine can be provided by the protein fraction as L-methionine. When D-methionine is included, the ratio d/l methionine is preferably <1 and more preferably 0-0.2, most preferably 0-0.05. Alpha-lactalbumin or whey fractions that comprise more than 40 wt % of alpha-lactalbumin were found to be suitable proteins, as well as proteins from egg, in particular egg white and mixtures thereof.

It is also advantageous to include melatonin in the product, especially in those products that are meant to be used in the evening. Melatonin upregulates certain enzymes that play an important role in the detoxification of radicals that are created in the highly firing neurons and that may play a role in the pathogenesis of the disorders mentioned above. Melatonin also can help to set and regulate the circadian rhythm, which can be very helpful in the treatment of sleeping disorders and depression. Melatonin can be included in an amount of 0.5-5 g per daily dosage.

Also adenosine can be used to set the circadian cycle; an amount of 50-1000 mg per daily serving is recommended.

Betaine, choline, methionine or their functional equivalents should be included in those situations that is suspected that the patient suffers from a lack of food components that provide methyl groups. Examples are the elderly or schizophrenic patients that often have very poor eating behaviour. Betaine is the preferred source because it also can serve as a precursor for choline that is useful for synthesis or myelin or repair of damaged neurons and because it has an excellent taste. Obviously also choline itself can be used. Betaine can be included in an amount of 30-4000 mg and preferably 50-600 mg per 100 kcal.

Vitamin K (phylloquinones, menaquinones and other naphthoquinones) or its functional equivalent is preferably included at a level of at least 8 µg, preferably at least 30 µg per 100 kcal. This is in particular preferable for infants and those patients that have been subjected to antibiotic treatment or cancer therapy or suffer from diarrhea for more than 2 days. For elderly persons, a daily minimum of 1 mg is found to be beneficial.

Other minerals, trace elements and vitamins can be included in amounts that comply with the recommendations as set by the National Research Council (US) or other official institutes.

The preferred amounts of all components depend on the group of patients for which the product is developed. Young infants would normally require lower amounts than adults; elderly suffering from a severe form of Alzheimer would normally benefit from less of the active components than a young adult that is suffering from the syndrome of Gilles de la Tourette.

Typical amounts per 100 kcal of the product are summarised in Table 1. The amounts as mentioned for one component in this table must be considered as a range that may occur independent of the ranges as mentioned for the other components

TABLE 1

| | Amounts per 100 kcal product | |
| --- | --- | --- |
| Component | Range | Preferred range |
| Digestible carbohydrates | 4-25 | 6-22 g |
| Folic acid | 44-4000 | 50-2000 µg |
| Vitamin B12 | 0.8-2000 | 1-1000* µg |
| Vitamin B6 | 50-10000 | 60-2000 µg |
| Riboflavin | 0.08-20 | 0.14-6 mg |
| Thiamine | 55-8000 | 70-4000 µg |
| Niacin | 0.55-60 | 1.4-25 mg niacin equivalents |
| Vitamin K | >8 | 30-90 µg |
| Taurine | 5-100 | 7-50 mg |
| Betaine | 30-4000 | 50-600 mg |
| Magnesium | 5-400 | 8-200 mg |

TABLE 1-continued

| | Amounts per 100 kcal product | |
|---|---|---|
| Component | Range | Preferred range |
| Zinc | 0.8-100 | 1-30 mg |
| Mg + Zn/Ca | >0.08 | >0.10 m/m |
| Mg + Zn/P | >0.20 | >0.26 m/m |
| Melatonin | 30-3000 | 60-800 mg |
| Tryptophan | 0.05-8 | 0.2-2* g |
| Adenosine | 1-1000 | 50-500 mg |
| Methionine | 50-1000 | 100-500 mg |

Note
*higher doses should preferably be given as a multi-unit serving of smaller doses.

Infant Formulae

When manufacturing infant formulae, several specific measures should be taken in order to support the metabolism of the infant and to meet regulations. These measures differ from those that have to be taken for diseased persons.

Energy density: The energy density of an infant formula is typically in the range of 62-73 kcal/100 ml liquid or reconstituted product. Preferably the energy density is in the range of 64-71 kcal/100 ml.

Proteins: Protein levels in a product can be determined with the classical Kjeldahl method. The result reflects the crude proteins that are present. For the purpose of this invention we define the protein level as the amount of real proteins plus the amount of amino acids, their salts and peptides; so non-proteinaceous compounds that comprise nitrogen are excluded. In the products of the invention the protein levels will be in the range of 1.0-3.0 g per 100 kcal, especially between 1.0 and 2.4 g/100 kcal, which allows complete satisfaction of the infants protein needs. An amount of 1.5-2.2 g/100 kcal is most preferred. The higher protein levels, such as from 2.0 or from 2.4 to 3.0 are especially suitable in combination with increased levels of folic acid, vitamin B6 and/or vitamin B12. Conventional proteins like those from cow's milk or soybeans can be used as basic protein sources, as they provide sufficient amounts of all essential amino acids but also branched-chain amino acids.

In order to increase the amount of L-tryptophan in the product, free L-tryptophan, or a functional equivalent thereof like tryptophan salts or tryptophan-rich peptides, can be supplemented. Preferably tryptophan is supplied predominantly in the form of an intact protein. At least 30 wt % of the protein reaction is preferably in the form of intact protein, more preferably 60-100, most preferably 80-100 wt %. If free L-tryptophan is used, special care is taken to remove all impurities that might cause toxic reactions. It is further preferred to use a tryptophan source that is stable under the conditions that the infant formula is manufactured. A suitable source is a tryptophan-rich protein or a hydrolysate or extract thereof. If proteins are used as ingredient, it is obvious that the levels of the large neutral amino acids (Tyr, Phe, Val, Leu, Ile) and threonine are relatively low. However they should not be that low, that the recommended daily intakes are not met. Examples of suitable proteins in this respect are acid whey, α-lactalbumin, egg protein and proteins from meat and wheat, and mixtures of two or more of these components. Acid whey protein or unhydrolysed α-lactalbumin are especially preferred, because of the excellent amino acid profile and the sustained release pattern in young children compared to hydrolysates thereof or compared to a combination of mixtures of alternative dairy products and suppleted sources of tryptophan, cysteine or arginine. Tryptophan should be present in the product in an amount of 1.6-3.5 g, especially 1.7-3.5 g per 100 g of the total protein component and preferably in an amount of 1.9-2.8 g/100 g protein.

The value of the ratio of the amounts in the product of tryptophan and the sum of the large neutral amino acids must be in the range 4.8-10 and preferably in the range 5.5-8.5/100, and most preferably 6.2-8.2/100. When threonine is also considered as a large neutral amino acid, the value of the ratio must be in the range 4.1-8.0 and preferably in the range 4.7-7.5.

In order to ensure sufficiently high levels of cysteine, whey proteins or egg proteins can be included in the formula. If whey proteins are used, acid whey is recommended, in order to avoid too high threonine levels. It is especially preferred to have a relatively high ratio of Cys/Trp in the range of 0.8-1.4, in order to support to optimally inclusion of cysteine in liver proteins and in glutathione, which is required for optimal growth and immune function.

In order to increase insulin response arginine or lysine can be supplied as L-forms of the free amino acid or as their functional equivalents. Functional equivalents of amino acids can for example be their salts, synthetic peptides, or proteins that are rich in the particular amino acid, or extracts or hydrolysates of these proteins. Also mixtures of proteins can be included. For example mixtures of 40% casein and 60% whey could be suppleted with the hydrochloric salts of L-tryptophan Carbohydrates: According to the invention, the amount of carbohydrates in the formula must be in the range of 9-15 g/100 kcal (35-60 en %), and preferably in the range of 11-14 g/100 kcal. This results in a carbohydrate content of 5.7-10.5 g per 100 ml of liquid or reconstituted product. The ratio of the amount of carbohydrates to the amount of tryptophan will exceed 20 and preferably 50, and go up to 940, preferably up to 450. The weight ratio of carbohydrates to protein is preferably from 5 to 14, most preferably from 6 to 12.

It is preferred to use, at least partly, maltodextrins, apart from the lactose that may be present in the formula. This will ensure a fast availability of glucose units in plasma and therefore a fast insulin response. However, it is preferred to include at least 50% of the carbohydrates as lactose, except in those cases that the product will be used by lactose-intolerant infants. If maltodextrins are used it is advantageous to use maltodextrins having a degree of hydrolysis of 10-15 dextrin equivalents, in order to decrease the sweetness of the product.

Folic acid: Folic acid can occur in nature in many forms. Typically it is suppleted to infant formulae as monoglutamate. Though according to the invention basically all functional equivalents of folic acid can be used, it is preferred to use the monoglutamate form for obtaining best bioavailability. It is essential to include at least 44 μg per 100 kcal. If higher amounts of folic acid are consumed, a larger group of infants will show an improved serotonin- and melatonin metabolism, even if the amounts of tryptophan are relatively low as in conventional infant formulae. This is especially true if the amount of folic acid is above 50 μg per 100 kcal and sufficient vitamin B12 is made available, as is the case when the formula is suppleted with more than 0.6 μg/100 kcal, as is indicated below.

Vitamin B12: Vitamin B12 is normally present in infant formula partially as a complex with dairy proteins and predominantly as suppleted cyanocobalamine. Before it is absorbed the complex has to be split in the stomach and the released cyanocobalamine has to bind to a factor that is released from the stomach. Once absorbed, cyanocobalamine or alternative forms have to be converted to methylcobalamine, before they can be used as a cofactor that catalyses the conversion of homocysteine to methionine. Both absorption and conversion of cyanocobalamine occur ineffectively in part of the population of young infants.

According to the invention it is therefore required to supplete at least 0.1 µg, and preferably more than 0.8 µg vitamin B12 per 100 kcal, preferably as hydroxycobalamine or a stabilised form, in order to support serotonin biosynthesis and metabolism effectively. Instead of vitamin B12, metabolic equivalents, i.e. compounds that lead to endogenous formation of vitamin B12, can also be used.

When indigestible carbohydrates are added to the product or other bifidogenic measures are taken, these are selected in such a way that the biosynthesis capacity of the gut flora is not imparted or even is stimulated.

Vitamin B6: Vitamin B6 is active in the cells as pyridoxal phosphate. However pyridoxine or pyridoxamine are frequently used as source of this vitamin, because of the stability of these compounds. Infants, especially those of young age, have a restricted capacity to convert these compounds to the active form. It has been found that a simple increase in the dose may decrease the intracellular pyridoxal phosphate levels. It is therefore preferred to include in the formula 50-130 µg vitamin B6 per 100 kcal. If higher amounts of vitamin B6 are suppleted, it is not recommended to use pyridoxine. Also mixtures of pyridoxamine or pyridoxal can be used.

Zinc: It is desirable that the amount of zinc is in the range of 0.7-2 mg/100 kcal, preferably from 0.7 to 1.0 mg/100 kcal. Zinc can be included as a zinc salt, such as zinc chloride or as a complex with amino acids or other components.

Niacin equivalents: Niacin functions in the human body as precursor of NAD and can be synthesised from tryptophan in the adult liver. This predominantly occurs when excess tryptophan is present. Thus tryptophan can also be used as a niacin equivalent (60 mg Trp=1 niacin equivalent). Biosynthesis of niacin is supported in the young child by the characteristic features of the composition as claimed. This permits the availability of sufficient niacin to support the metabolic processes in the child. These can be further supported by increase of the included amount of niacin to a level of 1.2-5 mg/100 kcal.

Apart from the essential components as indicated above, other microingredients may advantageously be included in a complete infant formula, according to EEC 91/321 or corresponding Regulation: these include: Betaine, choline; taurine, inositol, calcium, phosphorus, magnesium, iron, manganese, copper, iodine, sodium, potassium, chloride, selenium, fluoride, carnitine, nucleotides, cholesterol, vitamin A, vit. D, vit. E, vit K, thiamine, riboflavin, pantothenic acid, biotin, and ascorbic acid. Fats are included in the range of 40-57 en %. The composition of the fat can be selected from prior art compositions. Specially preferred are the ones that are disclosed in any of the earlier patents of patentee, e.g. EP-A-404058, EP-A-231904, EP-A-784437 and DE 19644518, which are incorporated by reference. For example, EP-A-404058, EP-A-231904, EP-A-784437 and DE 19644518 each discuss the addition of docosahexaenoic acid.

The essential fatty acids that are present must preferably have the cis-configuration. Alpha-linolenic acid (=ALA): 1.75-4.0% and linoleic acid (LA): 8-35% of total fatty acids; the ratio LA/ALA=5-16.

The product of the invention can have the form of liquid or a powder that can be reconstituted with water to produce a ready to feed formulation. It can also have the form of a meal that is used for weaning purposes or similar product evident to a person skilled in the art. The liquid products can be packaged in bottles, cartons and the like. The powdered products can be packaged under vacuum in packs, cans or sachets and other suitable forms that are known to a person skilled in the art.

It has been found that daily consumption of the infant formulae as described above results in the benefits as described below:
  improves feelings of well being by the infants,
  supporting regular eating and sleeping patterns
  helps to compensate for insufficient capacity of the metabolic systems, especially in the young infant
  decreases the prevalence of hyperbilirubinaemia
  decreases the allergic reaction in the young infant, in particular atopic reactions caused by non-food allergens.
  decreases postprandial plasma levels of phenylalanine in phenylketonuria patients
  consumption of these formulae results in plasma levels of amino acids that are more similar to those of infants, that are exclusively fed with human breast milk, compared to consumption of conventional formulae
  does not give negative side effects to the infant
  therefore improves health and immune status and supports growth of high quality
  has an excellent taste and can be produced at acceptable costs.

The products that are used by diseased or elderly adults should preferably meet some additional criteria.

Liquid nutritional products for adults can be supplements or provide complete nutrition. Typically complete nutrition aims to provide 1500-3500 kcal per day, depending on body weight and metabolic requirements [for being able to calculate product composition (gram per 100 kcal as provided by protein, lipid and digestible carbohydrate in the product) we assume consumption of 2000 kcal per day]. For this reason the complete liquid nutritional products according the invention preferably provide 0.9-5, and more preferably 1.0-3 kcal/ml. The products for supplementary reasons provide 0.3-3, preferably 0.4-1.8 kcal/ml.

Protein levels will vary between 2 and 12 g per 100 ml and the protein preferably provide 10-50, more preferably 12-40 en %. Lipid concentrations will vary between 0.3 and 10, preferably 1-8 g per 100 ml product, thus providing 3-50, preferably 10-40 en %. Digestible carbohydrate levels preferably vary between 4 and 25, more preferably 6-18 g per 100 ml, thus providing 30-60, preferably 33-55 en %.

For recalculating the composition of dry products from indicated liquid products we assume a concentration of 25 g dry matter per 100 ml.

For minerals and vitamins other than mentioned above, the recommended daily allowances (RDA) as defined by the US Food and Drug Administration are used as reference values. For complete products the included amount is 0.7-1.5 times the RDA value for an adult man. For products for supplementary use the amounts vary between 0 and 1.5 times the RDA value.

To the nutritional products that are intended to be used by immuno-compromised persons, like persons that suffer from severe virus infections, like HIV, influenza virus, cytomegalovirus or several Herpes viruses, or patients that suffer from tumors, were subjected to cancer therapy or are sensitive to developing metastasis, specific demands are to be set. For persons suffering from HIV an additional small amount of indoles, in particular 3-indolylacetate or indoles coupled to ascorbic acid, can beneficially be included. These amounts can amount to 1-10 wt % of the protein fraction.

In order to decrease satiating properties of the nutritional products according the invention, the inclusion of glycomacropeptide from milk is avoided. In particular when whey fractions are included the use of fractions of acid whey is aimed for.

EXAMPLES

Example 1

A liquid infant formula having the composition as presented in table 2 was prepared.

TABLE 2

Composition of liquid infant formula
Values are in mg per 100 ml, except where indicated differently.

| | |
|---|---|
| Protein (60% sweet whey, 40% casein) | 1400 |
| Added Trp | 10 |
| Added Arg | 10 |
| Lactose | 7500 |
| Maltodextrins (10-15 DE) | 1600 |
| Fat (EP-231904) | 3100 |
| Na | 18-25 |
| K | 60-100 |
| Cl | 40-60 |
| Ca | 50-85 |
| P | 20-50 |
| Mg | 4.5-6 |
| Fe | 0.5-0.9 |
| Zn | 0.6-1.3 |
| Cu | 40-60 µg |
| Mn | 5-20 µg |
| Se | 1.5-2.2 µg |
| I | 5-15 µg |
| Vitamin A | 80-90 RE |
| β-Carotene | 0-40 µg |
| Vitamin D | 1-1.6 µg |
| Vitamin E | 0.8-1.4 mg TE |
| Vitamin K | 4-20 µg |
| Thiamine | 35-45 µg |
| Riboflavin | 110-150 µg |
| Niacin | 0.7-1.0 mg NE |
| Pantothenate | 0.25-0.35 |
| Biotin | 1.5-1.7 µg |
| Ascorbic acid | 5-10 |
| Taurine | 4-7 |
| Folic acid (added as monoglutamate) | 25-32 µg |
| Vitamin B12 (added as hydroxycobalamine) | 0.4-0.7 µg |
| Vitamin B6 (added as pyridoxine) | 50-65 µg |

This product can be used for improving sleeping behaviour of young infants.

Example 2

Product to be Used for the Elderly or Toddlers as a Bedtime Drink

Powdered supplement packed in a can under nitrogen; 10 g to be reconstituted in fruit juice or milk before going to bed.
To 8 kg maltodextrin DET9 are added:
2.0 kg alpha-lactalbumin
50 mg melatonin
100 mg folic acid monoglutamate
25 mg cyanocobalamin
100 mg pyridoxal
100 mg riboflavin
60 mg thiamine.HCl
30 g zinc chloride. 12H2O
A proper aliquot is filled in the can, e.g. 400 g.

Example 3

Product to be Used for ADHD Infants or Alzheimer Patients

Powdered product packed in a 10 g sachet. The sachet is to be mixed with a portion of breakfast cereal and reconstituted in milk.

The powder is obtained by mixing:
9.5 kg Maltodextrin
100 mg folic acid
25 mg vit. B12
100 mg B6
100 mg B2
60 mg B1
1.0 g niacin
100 g betaine
300 g magnesium chloride
30 g zinc chloride
50 g adenosine
100 mg Vitamin K.

Example 4

Liquid Ready to Drink Nutritional Formula for Patients Suffering from Virus Infections or Cancer: Amounts of Active Components are Provided Per 100 Kcal

| | |
|---|---|
| Energy density | 20-65 kcal/100 ml |
| Protein | 2-4 g |
| alpha-lactalbumin enriched (>40 wt %) whey fraction comprising 2.3 wt % tryptophan | |
| Fat | 1-4 g |
| Carbohydrate | 10-20 g |
| About 10 wt % ribose -, about 70 wt % glucose -, about 15% galactose - and about 5 wt % maltose source: sources are at least partially oligo-/polymeric, amounts are all calculated as monosaccharide | |
| Fiber | 0.5-5 g |
| Folic acid | 400 µg |
| Vitamin B12 | 4 µg |
| Vitamin B6 | 4 mg |
| Vitamin B1 | 2 mg |
| Vitamin B3 (niacin) | 36 mg |
| Vitamin K | 160 mg |
| Vitamin A | 180 µg |
| Vitamin D | 1.28 µg |
| Vitamin B2 | 0.5 mg |
| Vitamin B5 (pantothenic acid) | 1.5 mg |
| Biotin | 7.5 µg |
| Vitamin C | 22 mg |
| Iron | 3.8 mg |
| Zinc | 7 mg |
| Copper | 1.0 mg |
| Manganese | 0.6 mg |
| Molybdenum | 11.8 µg |
| Selenium | 10 µg |
| Chromium | 9.2 µg |
| Iodine | 35 µg |
| Calcium | 266 mg |
| Phosphorus | 186 mg |
| Magnesium | 120 mg |
| Sodium | 30-180 mg |
| Potassium | 80-300 mg |
| Chloride | 30-180 mg |
| Betaine | 200 mg |

The invention claimed is:
1. A method for improving sleep behavior, insomnia and mood; and/or decreasing feelings of fear, pain, restlessness or depression, comprising administering to a person suffering from Alzheimer's Disease, Parkinson's Disease or schizophrenia and in need thereof an effective amount of a composition comprising a protein fraction, and digestible carbohydrates, wherein the composition comprises per 100 kcal:
more than 44 µg of folic acid,
more than 50 µg of vitamin B6,
more than 0.8 µg of vitamin B12,

5-400 mg of magnesium, 0.7-100 mg of zinc, and calcium, the weight ratio of magnesium plus zinc to calcium being higher than 0.08.

2. The method according to claim 1, wherein the composition further comprises at least one component selected from riboflavin, thiamine and niacin.

3. The method according to claim 1, in which the composition is a composition for complete nutrition comprising carbohydrates, fats and proteins.

4. The method according to claim 3, in which the fat comprise docosahexaenoic acid.

5. The method to claim 3, in which the composition further contains at least 0.55 mg of niacin and/or at least 0.08 mg of riboflavin and/or at least 55 μg of thiamine per 100 kcal.

6. The method according to claim 3, in which the composition further contains more than 50 mg of choline or betaine or the sum thereof.

7. The method according to claim 3, in which the composition further contains at least 50 mg of methionine per 100 kcal.

8. The according to claim 3, in which the composition wherein the weight ratio of tryptophan to the sum of the large neutral amino acids Tyr, Phe, Val, Leu and He is in the range of 4.8-10/100.

9. The method according to claim 3, in which the composition contains 9-15 g of carbohydrates per 100 kcal.

10. The method according to claim 1, comprising administering an amount of at least 200 μg of folic acid, at least 2 mg of vitamin B6, and at least 2 μg of vitamin B12 per daily dosage.

11. The method according to claim 10, comprising administering an amount of at least 300 μg of folic acid, at least 3.0 mg of vitamin B6, and at least 4.8 μg of vitamin B12 per daily dosage.

12. The method according to claim 1, wherein said protein fraction is selected form whey protein, acid whey and alpha-lactalbumin and mixtures thereof.

13. The method according to claim 1, wherein said protein fraction provides 0.4-4.0 g L-arginine and/or 0-1 g D-methionine isomers per 100 g of protein.

14. The method according to claim 1, comprising a protein fraction, which provides per 100 g of protein, 0.4-3.1 g L-arginine and/or 0.5-2.4 g L-methionine isomers.

15. The method according to claim 1 for improving sleep behavior, insomnia.

16. The method according to claim 1, for decreasing feelings of fear, pain, restlessness or depression.

* * * * *

UNITED STATES PATENT AND TRADEMARK OFFICE
CERTIFICATE OF CORRECTION

| | |
|---|---|
| PATENT NO. | : 8,450,347 B2 |
| APPLICATION NO. | : 12/033379 |
| DATED | : May 28, 2013 |
| INVENTOR(S) | : Hageman et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 975 days.

Signed and Sealed this
Nineteenth Day of May, 2015

Michelle K. Lee
*Director of the United States Patent and Trademark Office*